(12) United States Patent
Koay et al.

(10) Patent No.: US 8,758,346 B2
(45) Date of Patent: Jun. 24, 2014

(54) VARIABLE ANGLE COMPRESSION PLATE

(75) Inventors: Kenny Koay, West Chester, PA (US); Rene Haag, Berwyn, PA (US)

(73) Assignee: DePuy Synthes Products, LLC, Raynham, MA (US)

( * ) Notice: Subject to any disclaimer, the term of this patent is extended or adjusted under 35 U.S.C. 154(b) by 124 days.

(21) Appl. No.: 12/881,720

(22) Filed: Sep. 14, 2010

(65) Prior Publication Data

US 2011/0224671 A1   Sep. 15, 2011

Related U.S. Application Data

(60) Provisional application No. 61/242,102, filed on Sep. 14, 2009.

(51) Int. Cl.
*A61B 17/58* (2006.01)
*A61B 17/66* (2006.01)
*A61B 17/80* (2006.01)

(52) U.S. Cl.
USPC .............................. 606/70; 606/282; 606/291

(58) Field of Classification Search
USPC ........................................... 606/70, 280–299
See application file for complete search history.

(56) References Cited

U.S. PATENT DOCUMENTS

| | | | |
|---|---|---|---|
| 1,203,546 A | 10/1916 | Parsons | |
| 2,228,584 A | 1/1941 | Place | |
| 2,443,363 A | 6/1948 | Townsend et al. | |
| 2,477,430 A | 7/1949 | Swanstrom | |
| 2,846,701 A | 8/1958 | Bedford | |
| 3,229,743 A | 1/1966 | Derby | |
| 3,263,949 A | 8/1966 | Conrad | |
| 3,314,326 A | 4/1967 | Bedford | |
| 3,364,807 A | 1/1968 | Holton | |
| 3,388,732 A | 6/1968 | Holton | |
| 3,463,148 A | 8/1969 | Treace | |

(Continued)

FOREIGN PATENT DOCUMENTS

| CA | 1112803 | 11/1981 |
|---|---|---|
| CH | 611147 | 5/1979 |

(Continued)

OTHER PUBLICATIONS

"Multiple Offerings of Plates, Screws and Pegs", Small Bone Innovations, Inc., Dec. 2009, 2 pages.

(Continued)

*Primary Examiner* — Michael T Schaper
*Assistant Examiner* — Tracy Kamikawa
(74) *Attorney, Agent, or Firm* — Baker & Hostetler LLP

(57) ABSTRACT

A bone plate comprises a first surface and a second surface in combination with a first hole extending through the bone plate from the first surface to the second surface, the hole including a compression portion and a variable angle portion open to one another by a connecting space. The compression portion includes a sloping surface adapted to engage a head of a bone fixation element inserted thereinto so that the bone fixation element imparts a force to the bone plate to move the bone plate laterally relative to a portion of bone into which the bone fixation element is inserted. The variable angle portion includes a plurality of columns positioned about a circumference of a wall of the variable angle portion. The columns are separated from one another by a plurality of positioned between adjacent pairs of columns and including a plurality of protrusions extending radially inward therefrom.

31 Claims, 2 Drawing Sheets

(56) References Cited

U.S. PATENT DOCUMENTS

| | | | |
|---|---|---|---|
| 3,551,389 A | 12/1970 | Prince et al. | |
| 3,552,389 A | 1/1971 | Allgower et al. | |
| 3,630,261 A | 12/1971 | Gley | |
| 3,668,972 A | 6/1972 | Allgower et al. | |
| 3,688,972 A | 9/1972 | Mahon | |
| 3,695,618 A | 10/1972 | Woolley et al. | |
| 3,716,050 A | 2/1973 | Johnston | |
| 3,741,205 A | 6/1973 | Markolf et al. | |
| 3,744,488 A | 7/1973 | Cox | |
| 3,779,240 A | 12/1973 | Kondo | |
| 3,877,339 A | 4/1975 | Muenchinger | |
| RE28,841 E | 6/1976 | Allgower et al. | |
| 3,967,049 A | 6/1976 | Brandt | |
| 3,996,834 A | 12/1976 | Reynolds | |
| 4,029,091 A | 6/1977 | Von Bezold et al. | |
| 4,175,555 A | 11/1979 | Herbert | |
| 4,219,015 A | 8/1980 | Steinemann | |
| 4,263,904 A | 4/1981 | Judet | |
| 4,304,039 A | 12/1981 | Asmus | |
| 4,338,926 A | 7/1982 | Kummer et al. | |
| 4,355,198 A | 10/1982 | Gartland, Jr. | |
| 4,408,601 A | 10/1983 | Wenk | |
| 4,429,690 A | 2/1984 | Angelino-Pievani | |
| RE31,628 E | 7/1984 | Allgower et al. | |
| 4,484,570 A | 11/1984 | Sutter et al. | |
| 4,491,317 A | 1/1985 | Bansal | |
| 4,493,317 A | 1/1985 | Klaue | |
| 4,513,744 A * | 4/1985 | Klaue | 606/282 |
| 4,565,193 A | 1/1986 | Streli | |
| 4,612,923 A | 9/1986 | Kronenthal | |
| 4,630,985 A | 12/1986 | Simons | |
| 4,651,724 A | 3/1987 | Berentey et al. | |
| 4,683,878 A | 8/1987 | Carter | |
| 4,717,613 A | 1/1988 | Ottaviano | |
| 4,776,329 A | 10/1988 | Treharne | |
| 4,781,183 A | 11/1988 | Casey et al. | |
| 4,794,918 A | 1/1989 | Wolter | |
| 4,838,252 A | 6/1989 | Klaue | |
| 4,858,601 A | 8/1989 | Glisson | |
| 4,867,144 A | 9/1989 | Karas et al. | |
| 4,927,421 A | 5/1990 | Goble et al. | |
| 4,957,497 A | 9/1990 | Hoogland et al. | |
| 4,988,350 A | 1/1991 | Herzberg | |
| 5,002,544 A | 3/1991 | Klaue et al. | |
| 5,006,120 A | 4/1991 | Carter | |
| 5,027,904 A | 7/1991 | Miller et al. | |
| 5,039,265 A | 8/1991 | Rath et al. | |
| 5,041,113 A | 8/1991 | Biedermann et al. | |
| 5,041,114 A | 8/1991 | Chapman et al. | |
| 5,053,036 A | 10/1991 | Perren et al. | |
| 5,085,660 A | 2/1992 | Lin | |
| 5,108,399 A | 4/1992 | Eitenmuller et al. | |
| 5,129,901 A | 7/1992 | Decoste | |
| 5,147,361 A | 9/1992 | Ojima et al. | |
| 5,151,103 A | 9/1992 | Tepic et al. | |
| 5,190,544 A | 3/1993 | Chapman et al. | |
| 5,197,966 A | 3/1993 | Sommerkamp | |
| 5,261,910 A | 11/1993 | Warden et al. | |
| 5,269,784 A | 12/1993 | Mast | |
| 5,275,601 A | 1/1994 | Gogolewski et al. | |
| 5,304,180 A | 4/1994 | Slocum | |
| 5,306,275 A | 4/1994 | Bryan | |
| 5,324,290 A | 6/1994 | Zdeblick et al. | |
| 5,336,224 A | 8/1994 | Selman | |
| 5,360,448 A | 11/1994 | Thramann | |
| 5,364,398 A | 11/1994 | Chapman et al. | |
| 5,364,399 A | 11/1994 | Lowery et al. | |
| 5,403,136 A | 4/1995 | Mathys | |
| 5,429,641 A | 7/1995 | Gotfried | |
| 5,514,138 A | 5/1996 | McCarthy | |
| 5,534,032 A | 7/1996 | Hodorek | |
| 5,558,674 A | 9/1996 | Heggeness et al. | |
| 5,571,198 A | 11/1996 | Drucker et al. | |
| 5,591,168 A | 1/1997 | Judet et al. | |
| 5,601,551 A | 2/1997 | Taylor et al. | |
| 5,601,553 A | 2/1997 | Trebing et al. | |
| 5,607,426 A | 3/1997 | Ralph et al. | |
| 5,607,428 A | 3/1997 | Lin | |
| 5,620,445 A | 4/1997 | Brosnahan et al. | |
| 5,674,222 A | 10/1997 | Berger et al. | |
| 5,702,399 A | 12/1997 | Kilpela et al. | |
| 5,709,686 A | 1/1998 | Talos et al. | |
| 5,741,258 A | 4/1998 | Klaue et al. | |
| 5,749,872 A | 5/1998 | Kyle et al. | |
| 5,772,662 A | 6/1998 | Chapman et al. | |
| 5,785,713 A | 7/1998 | Jobe | |
| 5,810,823 A | 9/1998 | Klaue et al. | |
| 5,938,664 A | 8/1999 | Winquist et al. | |
| 5,954,722 A | 9/1999 | Bono | |
| 5,961,524 A | 10/1999 | Crombie | |
| 5,968,047 A | 10/1999 | Reed | |
| 5,976,141 A | 11/1999 | Haag | |
| 5,999,940 A | 12/1999 | Ranger | |
| 6,001,099 A | 12/1999 | Huebner | |
| 6,022,352 A | 2/2000 | Vandewalle | |
| 6,030,162 A | 2/2000 | Huebner | |
| 6,030,389 A * | 2/2000 | Wagner et al. | 606/71 |
| 6,096,040 A | 8/2000 | Esser | |
| 6,129,730 A | 10/2000 | Bono et al. | |
| 6,152,927 A | 11/2000 | Farris et al. | |
| 6,183,475 B1 | 2/2001 | Lester et al. | |
| 6,206,881 B1 | 3/2001 | Frigg et al. | |
| 6,228,085 B1 | 5/2001 | Theken et al. | |
| 6,261,291 B1 | 7/2001 | Talaber et al. | |
| 6,306,136 B1 | 10/2001 | Baccelli | |
| 6,322,562 B1 | 11/2001 | Wolter | |
| 6,342,055 B1 | 1/2002 | Eisermann | |
| 6,348,052 B1 | 2/2002 | Sammarco | |
| 6,364,882 B1 | 4/2002 | Orbay | |
| 6,423,064 B1 | 7/2002 | Kluger | |
| 6,440,135 B2 | 8/2002 | Orbay et al. | |
| 6,454,769 B2 | 9/2002 | Wagner et al. | |
| 6,454,770 B1 | 9/2002 | Klaue | |
| 6,468,278 B1 | 10/2002 | Muckter | |
| 6,525,525 B1 | 2/2003 | Azinger | |
| 6,527,776 B1 | 3/2003 | Michelson | |
| 6,565,569 B1 | 5/2003 | Assaker et al. | |
| 6,575,975 B2 | 6/2003 | Brace et al. | |
| D479,331 S | 9/2003 | Pike et al. | |
| 6,623,486 B1 | 9/2003 | Weaver et al. | |
| 6,669,701 B2 | 12/2003 | Steiner et al. | |
| 6,719,759 B2 | 4/2004 | Wagner et al. | |
| 6,730,091 B1 | 5/2004 | Pfefferle et al. | |
| 6,893,443 B2 | 5/2005 | Frigg et al. | |
| 6,955,677 B2 * | 10/2005 | Dahners | 606/287 |
| 6,974,461 B1 | 12/2005 | Wolter | |
| 7,044,953 B2 | 5/2006 | Capanni | |
| 7,128,744 B2 | 10/2006 | Weaver et al. | |
| 7,179,260 B2 | 2/2007 | Garlach et al. | |
| 7,229,445 B2 * | 6/2007 | Hayeck et al. | 606/70 |
| 7,309,340 B2 | 12/2007 | Fallin et al. | |
| 7,338,491 B2 | 3/2008 | Baker et al. | |
| 7,341,589 B2 | 3/2008 | Weaver et al. | |
| 7,354,441 B2 | 4/2008 | Frigg | |
| 7,537,596 B2 | 5/2009 | Jensen | |
| 7,637,928 B2 | 12/2009 | Fernandez | |
| 7,695,502 B2 | 4/2010 | Orbay et al. | |
| 7,766,916 B2 | 8/2010 | Leyden | |
| 8,075,561 B2 | 12/2011 | Wolter | |
| 8,118,846 B2 | 2/2012 | Leither et al. | |
| 8,337,535 B2 | 12/2012 | White et al. | |
| 2002/0156474 A1 | 10/2002 | Wack et al. | |
| 2004/0073218 A1 | 4/2004 | Dahners | |
| 2005/0015089 A1 | 1/2005 | Young et al. | |
| 2005/0107796 A1 | 5/2005 | Gerlach et al. | |
| 2005/0165400 A1 | 7/2005 | Fernandez | |
| 2005/0261688 A1 * | 11/2005 | Grady et al. | 606/69 |
| 2006/0004361 A1 | 1/2006 | Hayeck et al. | |
| 2006/0217722 A1 | 9/2006 | Dutoit et al. | |
| 2006/0235400 A1 * | 10/2006 | Schneider | 606/69 |
| 2007/0016205 A1 | 1/2007 | Beutter et al. | |
| 2007/0088360 A1 | 4/2007 | Orbay et al. | |
| 2007/0162016 A1 | 7/2007 | Matityahu | |
| 2007/0206244 A1 | 9/2007 | Kobayashi | |

(56) References Cited

U.S. PATENT DOCUMENTS

| | | | |
|---|---|---|---|
| 2008/0140130 A1* | 6/2008 | Chan et al. | 606/280 |
| 2008/0208259 A1 | 8/2008 | Gilbert et al. | |
| 2008/0234749 A1 | 9/2008 | Forstein | |
| 2008/0300637 A1 | 12/2008 | Austin et al. | |
| 2009/0018557 A1 | 1/2009 | Pisharodi | |
| 2009/0018588 A1 | 1/2009 | Eckhof et al. | |
| 2009/0076553 A1 | 3/2009 | Wolter | |
| 2009/0118768 A1* | 5/2009 | Sixto et al. | 606/280 |
| 2009/0143824 A1 | 6/2009 | Austin et al. | |
| 2009/0143825 A1 | 6/2009 | Graham et al. | |
| 2009/0312803 A1 | 12/2009 | Austin et al. | |
| 2010/0016858 A1 | 1/2010 | Michel | |
| 2010/0030277 A1 | 2/2010 | Haidukewych et al. | |
| 2010/0057086 A1 | 3/2010 | Price et al. | |
| 2010/0094357 A1 | 4/2010 | Wallenstein et al. | |
| 2010/0100134 A1 | 4/2010 | Mocanu | |
| 2010/0137919 A1 | 6/2010 | Wolter | |
| 2010/0274296 A1 | 10/2010 | Appenzeller et al. | |

FOREIGN PATENT DOCUMENTS

| | | |
|---|---|---|
| CH | 672245 | 11/1989 |
| CH | 675531 | 10/1990 |
| DE | 3442004 | 4/1986 |
| DE | 4341980 | 6/1995 |
| DE | 4343117 | 6/1995 |
| DE | 4438264 | 3/1996 |
| DE | 19629011 | 1/1998 |
| DE | 9321544 | 10/1999 |
| DE | 19832513 | 2/2000 |
| DE | 20309361 | 9/2003 |
| DE | 20317651 | 3/2004 |
| DE | 10 2005 042 766 | 1/2007 |
| DE | 10 2005 042766 | 1/2007 |
| EP | 0053999 | 6/1982 |
| EP | 158030 | 10/1985 |
| EP | 0207884 | 1/1987 |
| EP | 241914 | 10/1987 |
| EP | 266146 | 4/1988 |
| EP | 0360139 | 3/1990 |
| EP | 0410309 | 1/1991 |
| EP | 0515828 | 12/1992 |
| EP | 0530585 | 3/1993 |
| EP | 0848600 | 6/1998 |
| EP | 1468655 | 10/2004 |
| EP | 1604619 | 12/2005 |
| EP | 1658015 | 5/2006 |
| EP | 1712197 | 10/2006 |
| EP | 1741397 | 1/2007 |
| EP | 1767160 | 3/2007 |
| FR | 742618 | 3/1933 |
| FR | 2233973 | 2/1975 |
| FR | 2405705 | 5/1979 |
| FR | 2405706 | 5/1979 |
| FR | 2405062 | 6/1979 |
| FR | 2496429 | 6/1982 |
| FR | 2674118 | 9/1992 |
| GB | 997733 | 7/1965 |
| GB | 1237405 | 6/1971 |
| GB | 1250413 | 10/1971 |
| GB | 1312189 | 4/1973 |
| GB | 1385398 | 2/1975 |
| GB | 1575194 | 9/1980 |
| JP | 11299804 | 11/1992 |
| JP | H11/512004 | 10/1999 |
| JP | 2001/525701 | 12/2001 |
| JP | 2001/525702 | 12/2001 |
| JP | 2002/232185 | 8/2002 |
| JP | 2002/542875 | 12/2002 |
| JP | 2003/509107 | 3/2003 |
| SU | 1037911 | 8/1983 |
| SU | 1279626 | 12/1986 |
| WO | WO 87/00419 | 1/1987 |
| WO | WO 87/06982 | 11/1987 |
| WO | WO 88/03781 | 6/1988 |
| WO | WO 96/29948 | 10/1996 |
| WO | WO 97/09000 | 3/1997 |
| WO | WO 98/51226 | 11/1998 |
| WO | WO 00/53110 | 9/2000 |
| WO | WO 00/53111 | 9/2000 |
| WO | WO 00/66012 | 11/2000 |
| WO | WO 01/19267 | 3/2001 |
| WO | WO 01/54601 | 8/2001 |
| WO | WO 02/096309 | 12/2002 |
| WO | WO 2004/089233 | 10/2004 |
| WO | WO 2005/018472 | 3/2005 |
| WO | WO 2007/014279 | 2/2007 |
| WO | WO 2007/108734 | 9/2007 |
| WO | WO 2009/023666 | 2/2009 |
| WO | 2009/058969 | 5/2009 |
| WO | WO 2009/058969 | 5/2009 |

OTHER PUBLICATIONS

Stryker, "VariAx Distal Radius: Locking Plate System", www.osteosynthesis.stryker.com, 2006, 12 pages.
ACE Symmetry™ "Curves in All the Right Places", 1996, 3 pages.
"Cone Drive History and Double Enveloping Technology", http://conedrive.com/history/html., accessed Apr. 20, 2006, 9 pages.
English translation of International Patent Application No. PCT/CH03/00577: International Search Report dated Apr. 28, 2004, 6 pages.
International Patent Application No. PCT/CH03/00577: International Search Report dated Apr. 28, 2004, 3 pages.

* cited by examiner

VARIABLE ANGLE COMPRESSION PLATE

PRIORITY CLAIM

The present application claims priority to U.S. Provisional Application Ser. No. 61/242,102 entitled "Variable Angle Compression Plate" filed on Sep. 14, 2009, the entire disclosure of which is incorporated herein by reference.

FIELD OF THE INVENTION

The present application relates to a device for treating bone fractures and, in particular, to a bone plate including a combination variable angle and compression hole.

BACKGROUND

Bone plates are rigid plates utilized to stabilize damaged or weakened portions of bone such as fractures. These bone plates generally include openings adapted to receive bone fixation elements which anchor the plates to target portions of bone. Generally, each of these bone plate openings is configured to receive a single type of bone fixation element. However, in certain situations, it may be desirable to allow a user to select from a choice of bone fixation elements to apply through these bone plate holes.

SUMMARY OF THE INVENTION

The present invention is directed to a bone plate, comprising a first surface which, in an operative position, laces away from a bone to which the plate is to be mounted and a second surface which, in the operative position, faces a bone to which the plate is to be mounted in combination with a first hole extending through the bone plate from the first surface to the second surface, the hole including a compression portion and a variable angle portion open to one another by a connecting space, the compression portion including a sloping surface adapted to engage a head of a bone fixation element inserted thereinto so that the bone fixation element imparts a force to the bone plate to move the bone plate laterally relative to a portion of bone into which the bone fixation element is inserted, the variable angle portion including a plurality of columns positioned about a circumference of a wall of the variable angle portion, the columns being separated from one another by a plurality of gaps positioned between adjacent pairs of the columns and including a plurality of protrusions extending radially inward therefrom, wherein at least a portion of the connecting space is positioned between first and second ones of the columns.

DETAILED DESCRIPTION

Figure 1:
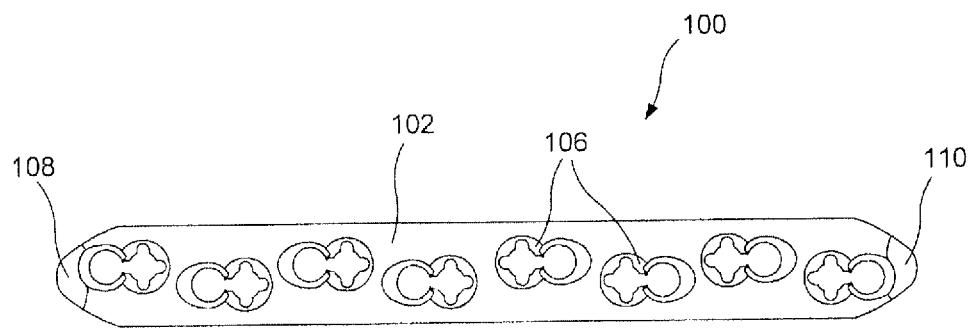
FIG. 1 shows a top plan view of a bone plate according to an exemplary embodiment of the present invention.

The present invention may be further understood with reference to the following description and the appended drawings, wherein like elements are referred to with the same reference numerals. The present invention relates to a device for treating bone fractures. In particular, exemplary embodiments of the present invention describe a bone plate including a combination variable angle and compression hole. It should be noted that the terms "proximal" and "distal" as used herein, are intended to describe a direction toward (proximal) and away from (distal) a surgeon or other user of the device.

Figure 2:
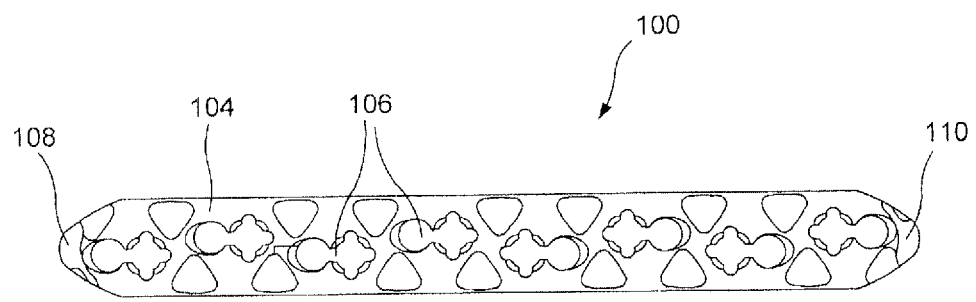
FIG. 2 shows a bottom plan view of the bone plate of FIG. 1.

As shown in FIGS. 1-2 a bone plate 100 according to an exemplary embodiment of the present invention comprises a first surface 102 facing away from a bone, a second surface 104 facing toward a bone and at least one combination hole 106 extending through the bone plate 100 from the first surface 102 to the second surface 104. The bone plate 100 extends longitudinally from a first end 108 to a second end 110 and may include any number of combination holes 106 along a length thereof. Although the bone plate 100 is only shown as including combination holes 106, it will be understood by those of skill in the art that the bone plate 100 may include other types of holes in addition to the combination hole 106.

Figure 3:
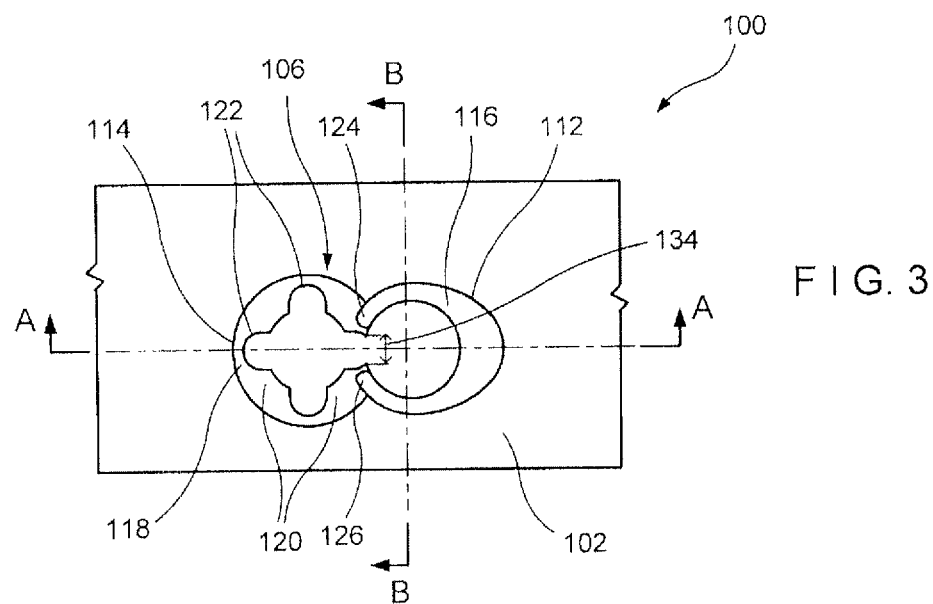
FIG. 3, shows an enlarged top plan view of an opening of the bone plate of FIG. 1.
Figure 4:
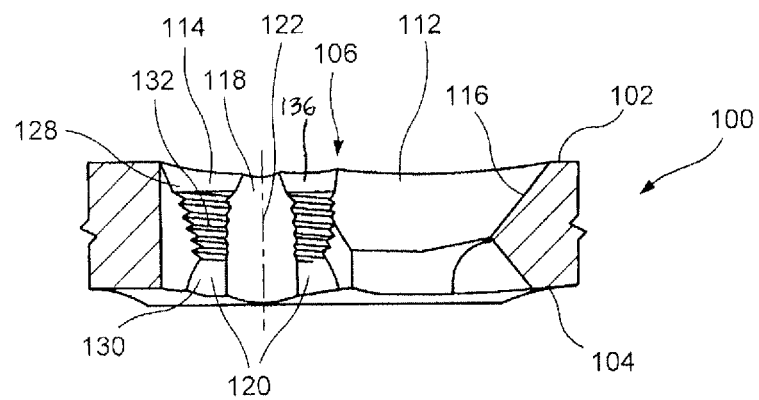
FIG. 4 shows a cross-sectional view of the opening of FIG. 3, along line A-A.
Figure 5:
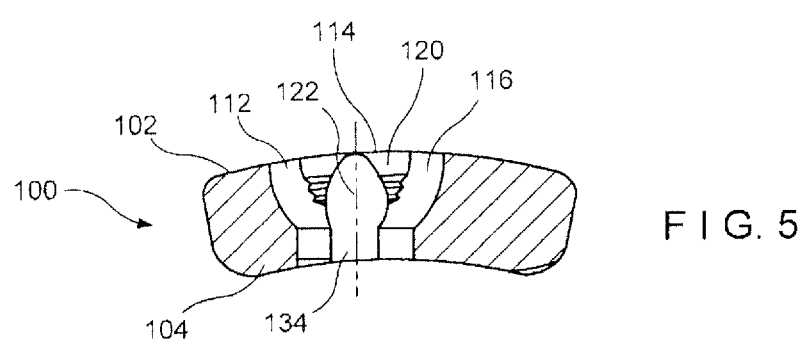
FIG. 5 shows a cross-sectional view of the opening of FIG. 3, along line B-B.

As shown in FIGS. 3-5, each combination hole 106 includes a first portion 112 and a second portion 114 which overlap and open to one another at a first contacting end 124 and a second contacting end 126. Thus, the first portion 112 and the second portion 114 are in communication with one another, forming a single combination hole 106. The first portion 112 is shaped and sized to receive a first type of bone fixation element (e.g., a screw including an non-threaded spherical head) such that engagement of the first portion 112 with the first type of bone fixation element provides compression of the bone fracture as would be understood by those skilled in the art while the second portion 114 is formed as a variable angle locking hole sized and shaped to receive a second type of bone fixation element (e.g., a screw including a threaded spherical head) at an angle relative to a central axis of the second portion 114 selected by a user to fix the bone plate 100 to the bone. The first and second portions 112, 114 may receive bone fixation elements including, for example, 1.5 mm to 7.3 mm spherical head screws.

It will be understood by those of skill in the art that other types of holes in addition to the combination hole 106 may be included in the bone plate 100. For example, the bone plate 100 may include combination holes 106 distributed along a shaft portion of the bone plate 100 and locking holes through a head portion of the bone plate 100. Alternatively, the bone plate 100 may include combination holes 106 distributed along an entire length of the bone plate 100 along with locking compression holes on the shaft portion and variable angle holes on the head portion. It will be understood by those of skill in the art that the bone plate 100 may include a variety of holes in a variety of patterns along a length thereof.

As discussed above, the first portion 112 forms a portion of an elongated opening, including a substantially concave recess 116 open to the first surface 102. The recess 116 is sized and shaped to engage the head of a compression bone screw such as, for example, a non-threaded spherical head of the first type of bone fixation element, to compress the bone fracture. The first portion 112 may be substantially similar to the any of the compression portions of holes described in U.S. Pat. No. 5,709,686 to Talos et al., U.S. Pat. No. 6,719,759 to Wagner et al. and U.S. Pat. No. 6,669,701 to Steiner et al. and U.S. Pat. No. 7,354,441 to Frigg, all of which are incorporated herein by reference. In a preferred embodiment, the first portion 112 may receive the first type of bone fixation element at an angle up to 50° relative to a central axis thereof in a longitudinal direction and at an angle up to 14° in a transverse direction. It will be understood by those of skill in the art, however, that a bone fixation element may be inserted through the first portion 112 of the hole 106 in a neutral position, in which the bone fixation element does not utilize the recess 116. In the neutral position, the bone fixation element does not provide compression to the bone, but merely anchors the bone plate 100 to the bone. The central axis of the first portion 112 may extend through a center thereof, substantially perpendicularly of the first surface 102.

The second portion 114 includes an opening that forms part of a circle with an inner surface 118 of the second portion 114 including a plurality of discrete columns 120 including protrusions 132 extending radially inward therefrom. The columns 120 are spaced from one another about the circumference of the inner surface 118. The columns 120 may be spaced equidistantly from one another with widths of the gaps 122 substantially equal to one another. However, it will be understood by those of skill in the art that the gaps 122 may also vary in width according to any desired pattern. Similarly, the columns 120 may be either substantially equal in width and size to one another or may vary in width and size so long as the columns 120 accommodate a head of the second type of bone fixation element. Adjacent columns 120 are separated from one another by gaps 122. The second portion 114 may also have a central axis, which extends through a center thereof, substantially perpendicular to the first surface 102. Thus, the second type of bone fixation element may be inserted through the second portion 114, at a user-selected angle relative to the central axis of the second portion 114.

In an exemplary embodiment the second portion 114 includes four columns 120, but may include any number of columns 120 and a corresponding number of gaps 122 therebetween. For example, the second portion 114 may include between 2 and 8 columns 120 such that the columns 120 may be separated from one another by 1 to 8 gaps 122. Each of the columns 120 extends radially inward (i.e., projects radially inward from the inner surface 118 toward a central axis of the second portion 114) into the opening of the second portion 114 and includes a proximal portion 128 extending distally into the second portion 114 from the first surface 102 to meet a distal portion 130 extending from the distal end of the proximal portion 128 to the second to the second surface 104. The protrusions 132 extend radially inward over at least a portion of the proximal portion 128. The protrusions 132 may include, for example, teeth, thread segments, pegs and spikes. In one exemplary embodiment, the protrusion 132 may include a threading formed of a plurality of circumferential projections separated from one another by a corresponding plurality of troughs along an axis of the second portion 114. The threading may be aligned so that, if the columns 120 were continued across the gaps 122, the threading would be a plurality of circular projections extending around the inner surface 118. In another embodiment, the protrusions 132 of the columns 120 is formed along a helical path so that, if continued across the gaps 122, the threading would be formed by a single projection extending helically around the inner surface 118 over a portion of the axial length of the second portion 114.

The proximal portion 128 is configured to receive the threaded head of the second type of bone fixation element so that the threading of the head engages the protrusions 132 of the columns 120 as the fixation element is inserted into the second portion 114. As would be understood by those skilled in the art, the second portion 114 is formed as a variable angle locking hole. Thus, the user selects an angle of insertion of the bone fixation element (i.e., an angle of a shaft of the bone fixation element relative to a central axis of the second portion 114) and inserts the bone fixation element into the second portion 114 until the protrusions 132 engage the threading of the head of the bone fixation element. The bone fixation element is then driven into the second portion 114 and the bone by screwing the bone fixation element thereinto until a desired position of the bone fixation element within the second portion 114 is achieved. As seen in FIG. 4, the proximal portion 128 decreases in diameter from the first surface 102 toward the second surface 104 until the distal end of the proximal portion 128 meets the proximal end of the distal portion 130. A diameter of the distal portion 130 then increases as it approaches the second surface 104 to accommodate a neck and/or proximal portion of a shaft of a bone fixation element inserted therethrough at an angle relative to the central axis of the second portion 114. Those skilled in the art will understand that the term diameter as used in this application refers to a minimum diameter of the second portion 114—e.g., a distance between diametrically opposed columns 120.

The proximal and distal portions 128, 130 are formed as relief cuts in the columns 120 to accommodate screw angulations. This geometry permits a bone fixation element to be locked within the second portion 114 at any angle within a permitted range of angulation between 0° and 15° relative to the central axis. However, those skilled in the art will understand that other ranges of angulation may be selected depending on the application.

In a further embodiment, the protrusions 132 extend along only a portion of the proximal portion 128 such that a proximal end 136 of the proximal portion 128 adjacent to the first surface 102 remains free of any protrusions 132, e.g., teeth, threads, pegs and/or spikes. Alternatively, the proximal end 136 may be adjacent the first surface 102 and proximal of the columns 120 such that a diameter of the proximal end 136 is larger than a diameter formed by the columns 120. The proximal end 136 may be sized and shaped for receiving a bone fixation element including a head portion that is non-threaded. Thus, the second portion 114 may be configured to receive bone fixation elements including both a threaded head (e.g., a locking screw) and a non-threaded head (e.g., a cortical screw).

The columns 120 are positioned about the circumference of the second portion 114 such that one of the gaps 122 overlaps with a space 134 between the first and second connecting ends 124, 126—i.e., with an opening between the first and second portions 112, 114. In a preferred embodiment the gap 120 is aligned with the space 134. As indicated above, the space 134 is formed by the intersection of the first and second portions 112, 114, respectively. Thus, as would be understood by those of skill in the art, due to the decreasing width of the proximal portion 128 from the first surface 102 toward the distal end of the proximal portion, a width of the space 134 will decrease in the same manner from the first surface 102 to the distal end of the proximal portion 128. The first and second portions 112, 114 are preferably positioned relative to one another so that a maximum width of the space 134 over the axial length of the threaded part of the proximal portion 128 is no greater than a width of the columns 120. Thus, the second portion 114 includes the same amount of threading it would have had even if there were no space 134 connecting it to the first portion 112. That is, in a preferred embodiment, the two columns 120 adjacent to the connecting points 124, 126 are separated by the space 134 rather than the gap 120 and are not reduced in size by the space 134, ensuring a secure engagement between the columns 120 and the head of the second type of bone fixation element.

It will be apparent to those skilled in the art that various modifications and variations can be made in the structure and the methodology of the present invention, without departing from the spirit or scope of the invention. Thus, it is intended that the present invention cover the modifications and variations of this invention provided that they come within the scope of the appended claims and their equivalents.

What is claimed is:

1. A bone plate, comprising:
a first surface which, in an operative position, faces away from a bone to which the plate is to be mounted;
a second surface which, in the operative position, faces the bone to which the plate is to be mounted; and
a hole extending through the bone plate from the first surface to the second surface, the hole including a compression portion, a variable angle portion, a central axis extending through the variable angle portion from the first surface to the second surface, and a connecting space that joins the variable angle portion to the compression portion such that the variable angle portion is open to the compression portion, the compression portion at least partially defining a first inner side wall, the first inner side wall defining first and second points each positioned adjacent the connecting space, the first and second points separated from each other by the connecting space, the first inner side wall being tapered about a circumference of the first inner side wall from the first point to the second point, the variable angle portion including a plurality of columns positioned about a circumference of a second inner side wall of the variable angle portion, each of the plurality of columns being separated from an adjacent one of the plurality of columns by a corresponding gap, each of the plurality of columns and each of the corresponding gaps defining a respective width measured: 1) in a circumferential direction about the central axis and 2) in a plane normal to the central axis, the respective width of each of the corresponding gaps being measured from one of the plurality of columns adjacent to the corresponding gap to another of the plurality of columns adjacent to the corresponding gap such that the respective width of each of the adjacent ones of the plurality of columns does not overlap with the respective width of the corresponding gap measured in the plane, each of the plurality of columns including a plurality of protrusions extending radially inward from the second inner side wall toward the central axis, wherein at least a portion of the connecting space is positioned between first and second ones of the plurality of columns such that the connecting space defines a maximum width between the first and second ones of the plurality of columns, such that the maximum width is no greater than the respective width of each of the corresponding gaps, the maximum width being measured 1) in the circumferential direction about the central axis and 2) in the plane.

2. The bone plate of claim 1, wherein the respective widths of each of the corresponding gaps are substantially equal to one another and the plurality of columns of the variable angle portion of the hole extends along a first portion of a length of the variable angle portion along the central axis.

3. The bone plate of claim 2, wherein adjacent ones of the plurality of columns are substantially equally spaced from one another about the circumference of the second inner side wall.

4. The bone plate of claim 1, wherein the variable angle portion includes a proximal portion that extends from a proximal end at the first surface to a distal end and a distal portion that extends from a proximal end at the distal end of the proximal portion to a distal end at the second surface, wherein a diameter of the proximal portion of the variable angle portion decreases through the proximal portion from a maximum at the proximal end of the proximal portion to a minimum at the distal end of the proximal portion.

5. The bone plate of claim 4, wherein a diameter of the distal portion of the variable angle portion increases from a minimum at the proximal end of the distal portion to a maximum at the distal end of the distal portion.

6. The bone plate of claim 1, wherein the maximum width of the connecting space is less than the respective width of each of the plurality of columns.

7. A bone plate, comprising:
a first surface which, in an operative position, faces away from a bone to which the plate is to be mounted;
a second surface which, in the operative position, faces the bone to which the plate is to be mounted; and
a hole extending through the bone plate from the first surface to the second surface, the hole including:
a first portion including a first opening in the first surface, the first opening defining an outer periphery of the first portion; and
a second portion, a central axis extending through the second portion from the first surface to the second surface, and a connecting space that joins the second portion to the first portion such that the second portion is open to the first portion, the second portion including a second opening in the first surface, the second opening being substantially circular and defining an outer periphery of the second portion, the first and second openings being positioned relative to each other such that the first opening is positioned outside the outer periphery of the second portion, the second portion further including a plurality of columns positioned about a circumference of a wall that at least partially defines the second portion, adjacent ones of the plurality of columns being separated from one another via a corresponding gap, each of the plurality of columns including protrusions extending from the wall toward the central axis such that the protrusions are configured to engage a threaded head of a bone fixation element at an angle within a range of angulations, each of the plurality of columns and each of the corresponding gaps defining a respective width measured: 1) in a direction perpendicular to a radially inward direction that intersects and is perpendicular to the central axis, and 2) in a plane normal to the central axis, such that the respective width of each of the plurality of columns does not overlap with the respective width of any of the corresponding gaps measured in the plane, at least a portion of the connecting space being positioned between first and second adjacent ones of the plurality of columns to form the gap corresponding thereto;
wherein the connecting space defines a maximum width between the first and second adjacent ones of the plurality of columns such that the maximum width is no greater than the respective width of each of the plurality of columns, the maximum width being measured: 1) in a direction perpendicular to the radially inward direction, and 2) in the plane.

8. The bone plate of claim 7, wherein the first portion includes a sloping surface adapted to engage a head of a bone fixation element inserted into the first portion so that the bone fixation element imparts a force to the bone plate to move the bone plate laterally relative to a portion of the bone into which the bone fixation element is inserted to compress a bone fracture.

9. The bone plate of claim 7, wherein the first portion is sized and shaped to receive a bone fixation element in a neutral position to anchor the bone plate to the bone.

10. The bone plate of claim 7, wherein the plurality of columns includes at least three columns and the second portion includes two corresponding gaps, each of the two corresponding gaps being spaced between respective adjacent ones of the plurality of columns, wherein the two corresponding gaps are substantially equal to one another in width and wherein the second portion is a variable angle portion, and the at least three columns of the variable angle portion; the width of each of the corresponding gaps of the hole extend along a first portion of a length of the variable angle portion along the central axis, the maximum width of the connecting space in the first portion of the length of the variable angle portion being no greater than the respective width of each of the two corresponding gaps.

11. The bone plate of claim 7, wherein the maximum width of the connecting space is less than the respective width of each of the corresponding gaps.

12. The bone plate of claim 7, wherein the wall is partially circular in shape at a position between the first surface and the second surface measured in a plane parallel to at least one of the first surface and the second surface.

13. The bone plate of claim 7, wherein the respective width of at least one of the first and second adjacent ones of the plurality of columns is equal to the respective width of each of the others of the plurality of columns.

14. The bone plate of claim 13, wherein the respective width of each of the first and second adjacent ones of the plurality of columns is equal to the respective width of each of the others of the plurality of columns.

15. The bone plate of claim 7, wherein each of the plurality of columns includes circumferentially opposed terminal ends, and the respective width of each of the plurality of columns is defined between the respective terminal ends.

16. The bone plate of claim 15, wherein the respective width of at least one of the first and second adjacent ones of the plurality of columns is equal to the respective width of each of the others of the plurality of columns.

17. The bone plate of claim 16, wherein the respective width of each of the first and second adjacent ones of the plurality of columns is equal to the respective width of each of the others of the plurality of columns.

18. A bone plate, comprising:
a first surface which, in an operative position, faces away from a bone to which the plate is to be mounted;
a second surface which, in the operative position, faces the bone to which the plate is to be mounted; and
a hole extending through the bone plate from the first surface to the second surface, the hole including:
a compression portion at least partially defining a first inner side wall, the first inner side wall defining a first portion that is tapered between the first surface and an intermediate point, and a second portion that is flared between the intermediate point and the second surface; and
a variable angle portion, a central axis extending through the variable angle portion from the first surface to the second surface, and a connecting space that joins the variable angle portion to the compression portion such that the variable angle portion is open to the compression portion, the variable angle portion including a plurality of columns positioned about a circumference of a second inner side wall of the variable angle portion, each of the plurality of columns being separated from an adjacent one of the plurality of columns by one of a plurality of gaps, each of the plurality of columns including a plurality of protrusions extending from the second inner side wall toward the central axis, each of the plurality of columns and each of the plurality of gaps defining a respective width measured: 1) in a direction perpendicular to a radially inward direction that intersects and is perpendicular to the central axis and 2) in a plane normal to the central axis, the respective width of each of the plurality of gaps being measured from a respective one of the plurality of columns to an adjacent one of the plurality of columns such that the respective width of each of the plurality of gaps does not overlap with the respective width of either the respective one of the plurality of columns or the adjacent one of the plurality of columns measured in the plane, wherein at least a portion of the connecting space is positioned between first and second ones of the plurality of columns such that the connecting space defines a maximum width between the first and second ones of the plurality of columns, such that the maximum width is no greater than the respective width of each of the plurality of gaps, the maximum width being measured: 1) in a direction perpendicular to the radially inward direction and 2) in the plane.

19. The bone plate of claim 18, wherein the first inner side wall defines a substantially partially spherical recess that extends through the first surface and is configured to slidingly engage a curved head of a bone fixation element inserted into the hole.

20. The bone plate of claim 18, wherein the respective widths of each of the plurality of gaps are substantially equal to one another, and wherein the plurality of columns of the variable angle portion of the hole extends along a first portion of a length of the variable angle portion along the central axis.

21. The bone plate of claim 20, wherein adjacent ones of the plurality of columns are substantially equally spaced from one another about the circumference of the second inner side wall.

22. The bone plate of claim 18, the variable angle portion including a proximal portion extending from a proximal end at the first surface to a distal end and a distal portion extending from a proximal end at the distal end of the proximal portion to a distal end at the second surface, wherein a diameter of the proximal portion of the variable angle portion decreases through the proximal portion from a maximum at the proximal end of the proximal portion to a minimum at the distal end of the proximal portion.

23. The bone plate of claim 22, wherein a diameter of the distal portion of the variable angle portion increases from a minimum at the proximal end of the distal portion to a maximum at the distal end of the distal portion.

24. The bone plate of claim 18, wherein the compression portion is configured to receive a bone fixation element at an angle ranging from between 0° to 50° relative to a central axis of the compression portion.

25. The bone plate of claim 18, wherein the compression portion is configured to receive a bone fixation element at an angle ranging from between 0° and 14° relative to a central axis of the compression portion.

26. The bone plate of claim 18, wherein the variable angle portion is configured to receive a bone fixation element at an angle of between 0° and 15° relative to the central axis of the variable angle portion.

27. The bone plate of claim 18, wherein the plurality of protrusions includes at least one of the group consisting of: teeth, thread segments, pegs and spikes.

28. The bone plate of claim 18, wherein the first inner side wall includes a sloping surface adapted to engage a head of a bone fixation element inserted into the compression portion so that the bone fixation element imparts a force to the bone plate to move the bone plate laterally relative to a portion of the bone into which the bone fixation element is inserted.

29. The bone plate of claim 18, wherein the maximum width of the connecting space is less than the respective width of each of the plurality of columns.

30. The bone plate of claim 18, wherein the second inner side wall is partially circular in shape at a position between the first surface and the second surface measured in a plane parallel to at least one of the first surface and the second surface.

31. The bone plate of claim 18, wherein the first portion is tapered from the first surface to the intermediate point, and the second portion is flared from the intermediate point to the second surface.

\* \* \* \* \*